(12) United States Patent
Peters et al.

(10) Patent No.: US 8,986,654 B2
(45) Date of Patent: Mar. 24, 2015

(54) LABELLED AND UN-LABELLED METHYL-PYRROLYL-OXADIAZOLYL-DIAZABICYCLONONANE DERIVATIVES AND THEIR MEDICAL USE

(75) Inventors: Dan Peters, Malmö (SE); Daniel B. Timmermann, Herlev (DK); Elsebet Østergaard Nielsen, København K (DK)

(73) Assignee: DanPET AB, Malmö (SE)

(*) Notice: Subject to any disclaimer, the term of this patent is extended or adjusted under 35 U.S.C. 154(b) by 0 days.

(21) Appl. No.: 14/111,462

(22) PCT Filed: Apr. 3, 2012

(86) PCT No.: PCT/EP2012/056029
§ 371 (c)(1),
(2), (4) Date: Oct. 11, 2013

(87) PCT Pub. No.: WO2012/139925
PCT Pub. Date: Oct. 18, 2012

(65) Prior Publication Data
US 2014/0030190 A1    Jan. 30, 2014

Related U.S. Application Data

(60) Provisional application No. 61/475,787, filed on Apr. 15, 2011.

(30) Foreign Application Priority Data
Apr. 15, 2011 (DK) .................. 2011 70179

(51) Int. Cl.
*A61K 51/00* (2006.01)
*A61M 36/14* (2006.01)
*A61K 51/04* (2006.01)
*C07D 471/08* (2006.01)

(52) U.S. Cl.
CPC .......... *A61K 51/0468* (2013.01); *C07D 471/08* (2013.01)
USPC .......................................... 424/1.89; 540/556

(58) Field of Classification Search
None
See application file for complete search history.

(56) References Cited

U.S. PATENT DOCUMENTS

| | | | |
|---|---|---|---|
| 6,844,337 B2 | 1/2005 | Galli et al. | |
| 7,223,753 B2 | 5/2007 | Peters et al. | |
| 7,662,808 B2 | 2/2010 | Peters et al. | |
| 7,807,667 B2 | 10/2010 | Peters et al. | |
| 8,106,042 B2 | 1/2012 | Peters et al. | |
| 2004/0266757 A1 | 12/2004 | Galli et al. | |
| 2005/0020599 A1 | 1/2005 | Galli et al. | |
| 2008/0292550 A1* | 11/2008 | Baerwolff et al. | 424/1.73 |
| 2010/0216780 A1 | 8/2010 | Peters et al. | |
| 2010/0280015 A1 | 11/2010 | Peters et al. | |
| 2011/0112078 A1 | 5/2011 | Peters et al. | |
| 2011/0263577 A1 | 10/2011 | Peters et al. | |
| 2011/0319397 A1 | 12/2011 | Peters et al. | |
| 2012/0003153 A1 | 1/2012 | Peters et al. | |
| 2012/0028968 A1 | 2/2012 | Peters et al. | |
| 2012/0238553 A1 | 9/2012 | Peters et al. | |
| 2012/0288443 A1* | 11/2012 | Peters et al. | 424/1.81 |
| 2013/0004428 A1 | 1/2013 | Peters et al. | |

FOREIGN PATENT DOCUMENTS

| | | |
|---|---|---|
| WO | WO 2004/029053 A1 | 4/2004 |
| WO | WO 2007/138037 A1 | 12/2007 |
| WO | WO 2007/138038 A1 | 12/2007 |
| WO | WO 2011/058002 A1 | 5/2011 |
| WO | WO 2011/073296 A1 | 6/2011 |

OTHER PUBLICATIONS

Deuther-Conrad, W. et al, "Molecular imaging of α7 nicotinic acetylcholine receptors: design and evaluation of the potent radioligand [18F]NS10743", European Journal of Nuclear Medicine and Molecular Imaging, No. 36, vol. 5, pp. 791-800, Jan. 10, 2009.
International Search Report, mailed Jun. 29, 2012, issued in PCT/EP2012/056029.
Muehllehner G. et al, Positron emission tomography, Physics in Medicine and Biology, No. 51, vol. 13, R117-R137, Jul. 7, 2006.
Written Opinion of the International Searching Authority, mailed Jun. 29, 2012, issued in PCT/EP2012/056029.

(Continued)

*Primary Examiner* — Michael G Hartley
*Assistant Examiner* — Sean R Donohue
(74) *Attorney, Agent, or Firm* — Birch, Stewart, Kolasch & Birch, LLP

(57) ABSTRACT

The present invention relates to certain labelled or un-labelled pyrrolyl-oxadiazolyl-diazabicyclononane derivatives and their medical use. Furthermore, the present invention relates to the use of said derivatives in their labelled form in diagnostic methods, in particular for in vivo receptor imaging (neuroimaging).

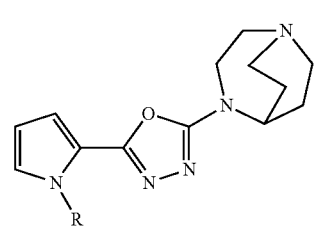

(I)

8 Claims, No Drawings

(56) References Cited

OTHER PUBLICATIONS

Notification Concerning Transmittal of International Preliminary Report on Patentability with Written Opinion for International Application No. PCT/EP2012/056029 dated Oct. 24, 2013.

Ettrup et al., "C-NS14492 as a Novel PET Radioligand for Imaging Cerebral α7 Nicotinic Acetylcholine Receptors: In Vivo Evaluation and Drug Occupancy Measurements," J. Nucl. Med. (2011), vol. 52, pp. 1449-1456.

* cited by examiner

LABELLED AND UN-LABELLED METHYL-PYRROLYL-OXADIAZOLYL-DIAZABICYCLONONANE DERIVATIVES AND THEIR MEDICAL USE

This application is the National Phase of PCT/EP2012/056029 filed on Apr. 3, 2012, which claims priority under 35 U.S.C. 119(e) to U.S. Provisional Application No. 61/475,787 filed on Apr. 15, 2011, and under U.S.C. 119(a) to Patent Application No. PA 2011 70179 filed in Denmark on Apr. 15, 2011, all of which are hereby expressly incorporated by reference into the present application.

TECHNICAL FIELD

The present invention relates to certain labelled and un-labelled methyl-pyrrolyl-oxadizolyl-diazabicyclononane derivatives and their medical use. Furthermore, the present invention relates to the use of said derivatives in their labelled form in diagnostic methods, in particular for in vivo receptor imaging (neuroimaging).

BACKGROUND ART

Neuroimaging is the use of certain technologies to measure a brain function or an aspect related to the functioning of certain parts of the brain, and enables the processing of information by centers in the brain to be visualized directly. Neuroimaging often requires the use of radioligands which have desirable properties for in vivo receptor imaging. These criteria include ease of labelling with positron-emitting radionucleotides, low rates of peripheral metabolism, high selectivity for brain regions holding the neuroreceptor of interest, and relatively high specific/non-specific binding ratios.

WO 2004/029053 WO 2007/138037 and WO 2007/138038 all describes oxadiazolyl-diazabicyclononane derivatives, which are found to be cholinergic ligands at the nicotinic acetylcholine receptors and modulators of the monoamine receptors and transporters. However, the labelled methyl-pyrrolyl-oxadiazole-diazabicyclononane derivatives of the present invention are not reported.

SUMMARY OF THE INVENTION

It is an object of the present invention to provide compounds that can be used in un-labelled form for medical uses, and in labelled form as a radiotracer or radio-labelled substance to monitor in vivo and in vitro levels of nicotinic acetylcholine receptors, and in particular the nicotinic α7 receptor subtype, by way of non-invasive determination of the localisation of such receptors (neuroimaging).

This object is solved by providing a labelled or un-labelled methyl-pyrrolyl-oxadiazole-diazabicyclononane derivative represented by Formula I

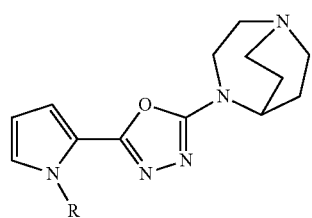

(I)

or a pharmaceutically acceptable salt thereof, wherein R represents a fluoro or $^{18}$F labelled methyl group.

In another aspect, the invention provides pharmaceutical compositions comprising a therapeutically effective amount of an un-labelled methyl-pyrrolyl-oxadiazole-diazabicyclononane derivative of the invention, or a pharmaceutically acceptable addition salt thereof, together with at least one pharmaceutically acceptable carrier or diluent.

In a third aspect, the invention provides pharmaceutical compositions comprising a diagnostically effective amount of a labelled methyl-pyrrolyl-oxadiazole-diazabicyclononane derivative of the invention, or a pharmaceutically acceptable addition salt thereof, together with at least one pharmaceutically acceptable carrier or diluent.

In a further aspect the invention provides methods for the non-invasive determination of the distribution of a tracer compound inside a whole, intact living animal or human body using a physical detection method, wherein the tracer compound is a compound of the invention, or a pharmaceutically acceptable salt thereof.

Other objects of the invention will be apparent to the person skilled in the art from the following detailed description and examples.

DETAILED DISCLOSURE OF THE INVENTION

Labelled and Un-Labelled methyl-pyrrolyl-oxadiazole-diazabicyclononane Derivatives In its first aspect the invention provides a labelled or un-labelled methyl-pyrrolyl-oxadiazole-diazabicyclononane derivative represented by Formula I

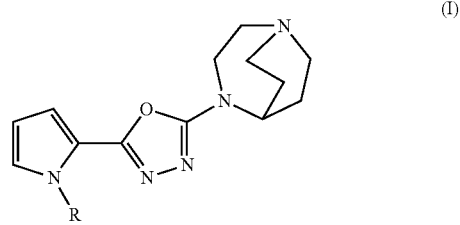

(I)

or a pharmaceutically acceptable salt thereof, wherein R represents a fluoro or $^{18}$F labelled methyl group, labelled by incorporation of one, two or three fluoro or $^{18}$F atoms at the methyl group.

In a most preferred embodiment the un-labelled methyl-pyrrolyl-oxadiazole-diazabicyclononane derivative of the invention is 2-(1,4-diazabicyclo[3.2.2]nonan-4-yl)-5-[1-(fluoromethyl)pyrrol-2-yl]-1,3,4-oxadiazole;
2-(1,4-diazabicyclo[3.2.2]nonan-4-yl)-5-[1-(difluoromethyl)pyrrol-2-yl]-1,3,4-oxadiazole; or
2-(1,4-diazabicyclo[3.2.2]nonan-4-yl)-5-[1-(trifluoromethyl)pyrrol-2-yl]-1,3,4-oxadiazole;
or a pharmaceutically acceptable salt thereof.

In a most preferred embodiment the labelled methyl-pyrrolyl-oxadiazole-diazabicyclononane derivative of the invention is 2-(1,4-diazabicyclo[3.2.2]nonan-4-yl)-5-[1-([$^{18}$F]fluoromethyl)pyrrol-2-yl]-1,3,4-oxadiazole;
2-(1,4-diazabicyclo[3.2.2]nonan-4-yl)-5-[1-([$^{18}$F]difluoromethyl)pyrrol-2-yl]-1,3,4-oxadiazole; or
2-(1,4-diazabicyclo[3.2.2]nonan-4-yl)-5-[1-[$^{18}$F](trifluoromethyl)pyrrol-2-yl]-1,3,4-oxadiazole;
or a pharmaceutically acceptable salt thereof.

Labelled Compounds

In the context of this invention a labelled compound has one or more atoms replaced by an atom having an atomic mass or mass number different from the atomic mass or mass number usually found in nature. Such labelling will allow easy quantitative detection of the compound in question, also designated the "hot ligand", in contrast to the corresponding un-labelled compound, designated the "cold ligand". Due to the relatively short half-life of the hot ligand, the hot ligand usually is prepared in situ from the cold ligand.

The labelled compounds of the invention may be useful as diagnostic tools, radio tracers, or monitoring agents in various diagnostic methods, and for in vivo receptor imaging.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

In a preferred embodiment the physical method for detecting the labelled isomer of the present invention is Position Emission Tomography (PET), Pharmaceutically Acceptable Salts The diazabicyclic aryl derivative of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Pharmaceutical Compositions

In another aspect the invention provides novel pharmaceutical compositions comprising a therapeutically effective amount of the methyl-pyrrolyl-oxadizolyl-diazabicyclononane derivative of the invention.

While a chemical compound of the invention for use in therapy may be administered in the form of the raw chemical compound, it is preferred to introduce the active ingredient, optionally in the form of a physiologically acceptable salt, or in the form of a prodrug, in a pharmaceutical composition together with one or more adjuvants, excipients, carriers, buffers, diluents, and/or other customary pharmaceutical auxiliaries.

In a preferred embodiment, the invention provides pharmaceutical compositions comprising the methyl-pyrrolyl-oxadizolyl-diazabicyclononane derivative of the invention, or a pharmaceutically acceptable salt or derivative thereof, together with one or more pharmaceutically acceptable carriers, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be prepared by any person skilled in the art, by use of standard methods and conventional techniques, appropriate to the desired formulation. When desired, compositions adapted to give sustained release of the active ingredient may be employed.

Further details on techniques for formulation and administration may be found in the latest edition of Remington's *Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Biological Activity

The compounds of the invention are found to be cholinergic ligands at the nicotinic acetylcholine receptors and modulators of the monoamine receptors and transporters. In a more preferred embodiment the invention is devoted to the provision novel ligands and modulators of the nicotinic receptors, which ligands and modulators are useful for the treatment of diseases or disorders related to the cholinergic receptors, and in particular the nicotinic acetylcholine receptor (nAChR). Preferred compounds of the invention show a pronounced nicotinic acetylcholine α7 receptor subtype selectivity.

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the invention may be useful for the treatment, prevention or alleviation of pain, mild or moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to postherpetic neuralgia, or to peripheral nerve injury.

In another preferred embodiment the compounds of the invention may be useful for the treatment, prevention or alleviation of diseases, disorders or conditions associated with smooth muscle contractions, convulsive disorders, angina pectoris, premature labour, convulsions, diarrhoea, asthma, epilepsy, tardive dyskinesia, hyperkinesia, premature ejaculation, or erectile difficulty.

In a third preferred embodiment the compounds of the invention may be useful for the treatment, prevention or alleviation of a neurodegenerative disorder, transient anoxia, or induced neuro-degeneration.

In a fourth preferred embodiment the compounds of the invention may be useful for the treatment, prevention or alleviation of an inflammatory disorder, inflammatory skin disorder, acne, rosacea, Crohn's disease, inflammatory bowel disease, ulcerative colitis, or diarrhoea.

In a fifth preferred embodiment the compounds of the invention may be useful for the treatment, prevention or alleviation of diabetic neuropathy, schizophrenia, cognitive or attention deficits related to schizophrenia, or depression.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines, benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 μM.

Preparation of Labelled methyl-pyrrolyl-oxadiazole-diazabicyclononane Derivatives The methyl-pyrrolyl-oxadiazole-diazabicyclononane derivatives of the invention may be prepared by conventional methods for chemical synthesis, e.g. those described in the working examples.

Labelling of the 1,4-diazabicyclo[3.2.2]nonane derivative of the invention may also be accomplished in analogy with the method described by e.g. Winnie Deuther-Conrad, Steffen Fischer, Achim Hiller, Elsebet Østergaard Nielsen, Daniel Brunicardi Timmermann, Jörg Steinbach, Osama Sabri, Dan Peters, Peter Brust: Molecular imaging of alpha-7 nicotinic acetylcholine receptors: design and evaluation of the potent radioligand [18F]NS10743; *Eur. J. Nucl. Med. Mol. Imaging.* 2009 36 791-800.

The end products of the reactions described herein may be isolated by conventional techniques, e.g. by extraction, crystallisation, distillation, chromatography, etc.

Neuroimaging

The methyl-pyrrolyl-oxadiazole-diazabicyclononane derivatives of the invention are useful as diagnostic tools or monitoring agents in various diagnostic methods, and in particular for in vivo receptor imaging (neuroimaging).

In another aspect of the invention, a method for the non-invasive determination of the distribution of a tracer compound inside a whole, intact living animal or human body using a physical detection method is provided. According to this method a tracer compound is a compound of the invention, or a pharmaceutically acceptable salt thereof, in labelled form.

In a preferred embodiment the physical detection method is selected from Positron Emission Tomography (PET), Single Photon Emission Computed Tomography (SPECT), Magnetic Resonance Spectroscopy (MRS), Magnetic Resonance Imaging (MRI), Computed Axial Tomography (CAT), Computed Tomography (CT), Functional Magnetic Resonance Imaging (fMRI), or combinations thereof.

In a more preferred embodiment the physical detection method is Positron Emission Tomography (PET).

Before conducting the method of the present invention, a diagnostically effective amount of a labelled compound of the invention is administered to a living body. The diagnostically effective amount of the labelled compound of the invention to be administered before conducting the in-vivo method for the present invention is within a range of from 0.1 ng to 100 mg per kg body weight, preferably within a range of from 1 ng to 10 mg per kg body weight.

EXAMPLES

All reactions involving air sensitive reagents or intermediates were performed under nitrogen and in anhydrous solvents. Magnesium sulfate was used as drying agent in the workup-procedures and solvents were evaporated under reduced pressure.

Example 1

Preparatory Example 1,4-Diazabicyclo[3.2.2]nonane (Intermediate compound)

The title compound was prepared according to *J. Med. Chem.* 1993 36 2311-2320 (and according to the slightly modified method described below).

1,4-Diazabicyclo[3.2.2]nonane (Intermediate compound)

To the solution of 1,4-diazabicyclo[3.2.2]nonan-3-one (15.8 g; 113 mmol) in absolute dioxane (130 ml) LiAlH$_4$ (4.9 g; 130 mmol) was added under argon. The mixture was refluxed for 6 h and then allowed to reach room temperature. To the reaction mixture water (5 ml in 10 ml of dioxane) was added by drops, the mixture was stirred for 0.5 hour and then filtered off via glass filter. The solvent was evaporated and the residue was distilled using Kugelrohr apparatus at 90° C. (0.1 mbar) to yield 1,4-diazabicyclo[3.2.2]nonane (11.1 g; 78%) as colourless hygroscopic material.

1,4-Diazabicyclo[3.2.2]nonan-3-one (Intermediate compound)

To the solution of 3-quinuclidinone hydrochloride (45 g; 278 mmol) in 90 ml of water hydroxylamine hydrochloride (21 g; 302 mmol) and sodium acetate (CH$_3$COONax3H$_2$O; 83 g; 610 mmol) were added, the mixture was stirred at 70° C. for 1 hour and then cooled to 0° C. The separated crystalline material was filtered off (without washing) and dried in vacuo to yield 40.0 g of oxime.

The 3-quinuclidinone oxime (40.0 g) was added during 2 hours by small portions preheated to 120° C. polyphosphoric acid (190 g). The temperature of the solution during the reaction was kept at 130° C. After addition of all oxime the solution was stirred for 20 minutes at the same temperature, and was allowed to reach room temperature. The acidic mixture was neutralized by a solution of potassium carbonate (500 g in 300 ml of water), transferred into 2000 ml flask, diluted with 300 ml of water and extracted with chloroform (3×600 ml). The combined organic extracts were dried with sodium sulphate, the solvent evaporated and the solid residue dried up in vacuo to yield 30.0 g (77%) of the mixture of lactams.

Crystallization of the obtained mixture from 1,4-dioxane (220 ml) gave 15.8 g (40.5%) of 1,4-diazabicyclo[3.2.2]nonan-3-one as colourless large crystals with mp. 211-212° C.

2-(1,4-diazabicyclo[3.2.2]nonan-4-yl)-5-[1-(fluoromethyl)pyrrol-2-yl]-1,3,4-oxadiazole (Compound 1)

May be prepared according to Methods A-D from 5-[1-(fluoromethyl)pyrrol-2-yl]-1,3,4-oxadiazole-2-thiol (Method A), from 1-(fluoromethyl)pyrrole-2-carbohydrazide (Method B), from methyl 1-(fluoromethyl)pyrrole-2-carboxylate (Method C), and from methyl 1H-pyrrole-2-carboxylate (Method D).

2-(1,4-diazabicyclo[3.2.2]nonan-4-yl)-5-[1-(difluoromethyl)pyrrol-2-yl]-1,3,4-oxadiazole (Compound 2)

May be prepared according to Methods A-D from 5-[1-(difluoromethyl)pyrrol-2-yl]-1,3,4-oxadiazole-2-thiol (Method A), from 1-(difluoromethyl)pyrrole-2-carbohydrazide (Method B), from methyl 1-(trifluoromethyl)pyrrole-2-carboxylate (Method C), and from methyl 1H-pyrrole-2-carboxylate (Method D).

Method D yields 77.8%, and LC-ESI-HRMS of [M+H]+ shows 310.14789 Da. Calc. 310.147396 Da, dev. 1.6 ppm.

2-(1,4-diazabicyclo[3.2.2]nonan-4-yl)-5-[1-(trifluoromethyl)pyrrol-2-yl]-1,3,4-oxadiazole (Compound 3)

May be prepared according to Methods A-D from 5-[1-(trifluoromethyl)pyrrol-2-yl]-1,3,4-oxadiazole-2-thiol (Method A), from 1-(trifluoromethyl)pyrrole-2-carbohydrazide (Method B), from methyl 1-(trifluoromethyl)pyrrole-2-carboxylate (Method C), and from methyl 1H-pyrrole-2-carboxylate (Method D).

2-(1,4-diazabicyclo[3.2.2]nonan-4-yl)-5-[1-([$^{18}$F] fluoromethyl)pyrrol-2-yl]-1,3,4-oxadiazole (Compound 1')

May be prepared in situ from 2-(1,4-diazabicyclo[3.2.2] nonan-4-yl)-5-(1H-pyrrol-2-yl)-1,3,4-oxadiazole free base (Compound A) and 1-[$^{18}$F]fluoro-1-iodomethane; or alternatively from 2-(1,4-diazabicyclo[3.2.2]nonan-4-yl)-5-(1H-pyrrol-2-yl)-1,3,4-oxadiazole free base (Compound A) and 1-[$^{18}$F]fluoro-1-methyltriflate.

2-(1,4-diazabicyclo[3.2.2]nonan-4-yl)-5-[1-([$^{18}$F] difluoromethyl)pyrrol-2-yl]-1,3,4-oxadiazole (Compound 2')

May be prepared in situ from 2-(1,4-diazabicyclo[3.2.2] nonan-4-yl)-5-(1H-pyrrol-2-yl)-1,3,4-oxadiazole free base (Compound A) and 1-[$^{18}$F]difluoro-1-iodomethane; or alternatively from 2-(1,4-diazabicyclo[3.2.2]nonan-4-yl)-5-(1H-pyrrol-2-yl)-1,3,4-oxadiazole free base (Compound A) and 1-[$^{18}$F]difluoro-1-methyltriflate.

2-(1,4-diazabicyclo[3.2.2]nonan-4-yl)-5-[1-[$^{18}$F] (trifluoromethyl)pyrrol-2-yl]-1,3,4-oxadiazole (Compound 3')

May be prepared in situ from 2-(1,4-diazabicyclo[3.2.2] nonan-4-yl)-5-(1H-pyrrol-2-yl)-1,3,4-oxadiazole free base (Compound A) and 1-[$^{18}$F]trifluoro-1-iodomethane; or alternatively from 2-(1,4-diazabicyclo[3.2.2]nonan-4-yl)-5-(1H-pyrrol-2-yl)-1,3,4-oxadiazole free base (Compound A) and 1-[$^{18}$F]trifluoro-1-methyltriflate.

Method A 2-(1,4-Diazabicyclo[3.2.2]nonan-4-yl)-5-(1H-pyrrol-2-yl)-1,3,4-oxadiazole free base (Compound A)

A mixture of 1,4-diazabicyclo[3.2.2]nonane (3.02 g, 23.9 mmol), 5-(1H-pyrrol-2-yl)-1,3,4-oxadiazole-2-thiol (Compound B) (5.0 g, 20.9 mmol) and 1-pentanol (50 ml) was stirred for 15 h. The mixture was solved in chloroform and was filtered through celite. The mixture was purified three times by silica gel chromatography, using chloroform, methanol and aqueous ammonia (89:10:1). The product was dried and evaporated. Yield 382 mg (6%). LC-ESI-HRMS of [M+H]+ shows 260.15096 Da. Calc. 260.15059 Da, dev. 1.4 ppm.

Method B 5-(1H-pyrrol-2-yl)-1,3,4-oxadiazole-2-thiol (Compound B)

Potassium hydroxide (4.78 g, 85.3 mmol) was solved in methanol (125 ml). 1H-pyrrole-2-carbohydrazide (Compound C) (9.7 g, 77.5 mmol) was added and the mixture was stirred for 30 minutes. Carbon disulfide (14.7 g, 193.8 mmol) was added to the mixture followed by stirring at 65° C. for 15 h. Another equivalent of carbon disulfide (5.90 g, 77.5 mmol) was added followed by stirring at 65° C. for 4 days. Aqueous hydrochloric acid (1 M) was added in excess quantity, the mixture was stirred and filtered and washed with aqueous hydrochloric acid. Yield 10 g (77%).

Method C 1H-pyrrole-2-carbohydrazide (Compound C)

Hydrazine monohydrate (31.0, 620 mmol) was added to a mixture of methyl 1H-pyrrole-2-carboxylate and methanol (100 ml) followed by stirring at 65° C. for 15 h. The mixture was evaporated and the product was isolated as a crystalline solid.

Method D

Methyl 1-(difluoromethyl)pyrrole-2-carboxylate (Compound D)

Was prepared from stirred a mixture of methyl 1H-pyrrole-2-carboxylate (3.04 g, 23.5 mmol), difluoroiodomethane (4.4 g, 24.7 mmol) and DMF (40 ml). Sodium hydride (1.41 g, 35.2 mmol) was added in portions during 30 minutes. The mixture was stirred for additional 15 minutes. Water (50 ml) was added and the mixture was extracted with dichloromethane. The mixture was purified by silica gel chromatography, using dichloromethane as solvent. The product was dried and evaporated. Yield 3.21 g (78%).

The invention claimed is:

1. A labelled or un-labelled methyl-pyrrolyl-oxadiazole-diazabicyclononane derivative represented by Formula I

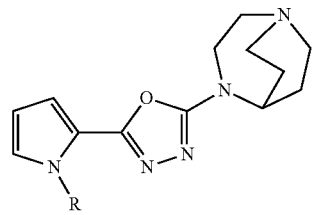

or a pharmaceutically acceptable salt thereof, wherein R represents an un-labelled difluoro-methyl group or a difluoro-methyl group labelled by incorporating two $^{18}$F at the methyl group.

2. The un-labelled methyl-pyrrolyl-oxadiazole-diazabicyclononane derivative of claim 1, which is
2-(1,4-diazabicyclo[3.2.2]nonan-4-yl)-5-[1-(difluoromethyl)pyrrol-2-yl]-1,3,4-oxadiazole; or
or a pharmaceutically acceptable salt thereof.

3. The labelled methyl-pyrrolyl-oxadiazole-diazabicyclononane derivative of claim 1, which is
2-(1,4-diazabicyclo[3.2.2]nonan-4-yl)-5-[1-([$^{18}$F]difluoromethyl)pyrrol-2-yl]-1,3,4-oxadiazole; or
or a pharmaceutically acceptable salt thereof.

4. A pharmaceutical composition comprising a diagnostically effective amount of a labelled or un-labelled methyl-pyrrolyl-oxadiazole-diazabicyclononane derivative of any one of claims 1-3, or a pharmaceutically acceptable addition salt thereof, together with at least one pharmaceutically acceptable carrier or diluent.

5. A method for non-invasive determination of the localization of nicotinic acetylcholine receptors, comprising the steps of:
administering the labelled methyl-pyrrolyl-oxadiazole-diazabicyclononane derivative according to claim 1, or a pharmaceutically acceptable salt thereof as the tracer compound; and
monitoring in vivo levels of said nicotinic acetylcholine receptors with the labelled methyl-pyrrolyl-oxadiazole-diazabicyclononane derivative of claim 1 as a radiotracer, or a pharmaceutically acceptable salt thereof.

6. The method according to claim 5, wherein the nicotinic acetylcholine receptors are of the nicotinic α7 receptor subtype.

7. A method for the non-invasive determination of the distribution of a tracer compound inside a whole, intact living animal or human body, comprising the steps of:
administering the labelled methyl-pyrrolyl-oxadiazole-diazabicyclononane derivative according to claim 1, or a pharmaceutically acceptable salt thereof as the tracer compound; and
detecting the labelled methyl-pyrrolyl-oxadiazole-diazabicyclononane derivative, or a pharmaceutically acceptable salt thereof, using a physical detection method.

8. The method according to claim 7, wherein the physical detection method is positron emission tomography (PET).

* * * * *